United States Patent [19]

Manook et al.

[11] Patent Number: 5,420,432
[45] Date of Patent: May 30, 1995

[54] ORGANIC POLLUTANT MONITOR

[75] Inventors: Boghos A. Manook, Wiltshire; Philip G. Morgan, West Glamorgan, both of England

[73] Assignee: Welsh Water Enterprises Limited, Gwent., England

[21] Appl. No.: 119,116
[22] PCT Filed: Mar. 18, 1992
[86] PCT No.: PCT/GB92/00477
 § 371 Date: Oct. 20, 1993
 § 102(e) Date: Oct. 20, 1993
[87] PCT Pub. No.: WO92/16828
 PCT Pub. Date: Oct. 1, 1992

[30] Foreign Application Priority Data

Mar. 19, 1991 [GB] United Kingdom ............ 9105737
Oct. 30, 1991 [GB] United Kingdom ............ 9123057

[51] Int. Cl.$^6$ .................... G01N 21/17; G01N 21/01
[52] U.S. Cl. .................................... 250/373; 73/863.23
[58] Field of Search ...................... 250/373; 73/863.23

[56] References Cited

U.S. PATENT DOCUMENTS

| | | | |
|---|---|---|---|
| 3,892,485 | 7/1975 | Merritt et al. | 356/339 |
| 3,917,945 | 11/1975 | Sema et al. | 250/301 |
| 4,152,075 | 5/1979 | Rellstab et al. | 356/435 |
| 4,361,403 | 11/1982 | Loos | 356/336 |
| 4,587,835 | 5/1986 | Adams | 73/23.37 |
| 4,726,931 | 2/1988 | Benet et al. | 422/81 |
| 4,775,794 | 10/1988 | Behmann | 250/373 |
| 4,994,671 | 2/1991 | Safinya et al. | 250/255 |

FOREIGN PATENT DOCUMENTS

| | | | |
|---|---|---|---|
| 0059593 | 9/1982 | European Pat. Off. | |
| 2709866 | 9/1977 | Germany | 250/373 |
| 4-242142 | 8/1992 | Japan | 73/863.23 |
| 2105028 | 3/1983 | United Kingdom | |
| 2127537 | 4/1984 | United Kingdom | |
| 2166234 | 4/1986 | United Kingdom | |
| 2212261 | 7/1989 | United Kingdom | |
| 9123057 | 1/1992 | United Kingdom | |
| WO87/03091 | 5/1987 | WIPO | |
| 92/00477 | 12/1992 | WIPO | |

OTHER PUBLICATIONS

Yozo Morita, Takeshi Goto, Koji Omatsu, Hideyuki Miki, Masakatsu Taniguchi and Masao Tanaka, "Shimadzu Organic Pollution Monitor Model UVM-401." *Shimadzu Review* (Japan) vol. 37, No. 4 (Dec. 1980) pp. 15–20.
Patent Abstracts of Japan, vol. 7, No. 168, P212, abstracts of JP58-73847, (Fuji Denki Seizo K.K.) 1983 May 4.
Horiba —Model OPSA-100 (Organic Pollutant Monitor), Bulletin: HRE-1840D.
Horiba—Model OSPA-120 (Organic Pollutant Monitor), Bulletin HRE-1871A.
pHOX-Model OPM-500 (Organic Pollution Monitors).
Sigrist-Model KA-100J (Sigrist Absorptiometer).

*Primary Examiner*—Constantine Hannaher
*Attorney, Agent, or Firm*—Nixon & Vanderhye

[57] ABSTRACT

An ultra-violet absorbence-based monitor for on-line monitoring of organic pollution in water at on-site locations measure the reduction in UV light passed through a sample and also makes measurements to provide indications of the amounts of visible light absorbed by, and scattered by, the samples respectively. The amount of organic matter is determined from the measured reduction in UV light by a calculation in which the results of the other measurements are used for compensation purposes. The sampling apparatus comprises a buoyant sampling head with an inlet port submerged beneath the water surface.

30 Claims, 4 Drawing Sheets

ORGANIC POLLUTANT MONITOR

BACKGROUND OF THE INVENTION

1. Field of the Invention

This invention relates to an ultra-violet (UV) absorbence-based monitor for measuring the amount of organic pollution in a liquid, and is of particular application for on-line monitoring of water quality at locations, such as, for example, industrial or water treatment plant effluent outlets, rivers or reservoirs.

2. Related Art

A number of methods are available for determining the biological or organic pollution in water, involving the measurement of parameters such as BOD (biochemical oxygen demand), TOC (total organic carbon) or COD (chemical oxygen demand). The parameter that is usually of most interest is the BOD. Traditionally, the BOD of a liquid sample has been determined in a laboratory test in which a liquid sample is incubated in the presence of microorganisms for 5 days at 20° C. in the dark, dissolved oxygen consumed by the micro-organisms being measured and expressed as BOD in mg $O_2$/L of sample. The 5 day BOD test is a standard test laid down by a Royal Commission in 1910. It gives results that are repeatable either for different samples of the same liquid, or for the same liquid tested at different laboratories, within about 15 per cent, but it is, however, exceedingly cumbersome and slow; hence, a need has arisen for a method of continuously monitoring BOD on-line at influent or effluent locations both to meet legislative requirements and to provide process control information.

A number of on-line, continuous BOD monitors have recently been developed, based on a variety of techniques. One such monitor is an on-line continuous BOD monitor based on the respiratory method. Although that monitor is capable of producing similar results to the laboratory test over a three minute rather than five day period, it is prohibitively expensive.

Alternative monitors include the cheaper UV absorbence-based monitors, which are simple to use and maintain. These are based on the principle that a particular substance will absorb light of a particular wavelength (or wavelengths), so that the reduction in intensity of light of that wavelength, when transmitted through a sample containing the substance, can be related to the concentration of that substance. Aromatic organic compounds, and other organic compounds that have conjugated double bonds, absorb light in the UV wavelength region and research has shown that absorbence measurements taken in that region, and in particular at 254 nm, can be related to BOD (and also to TOC and COD).

The performance of existing UV based-absorbence monitors has, however, been disappointing in that the absorption readings (usually at 254 nm) have been shown to be unreliable as an indication of organic pollution due to their dependence on other, unknown factors. Past attempts have been made to compensate only for turbidity in liquid samples. While these monitors have proved accurate and reliable, there being a good correlation between their results and the standard 5-day BOD test, this has only been because the use of such monitors has been confined to specific locations, liquid types and to short sampling periods (less than one day), with thorough testing first being carried out in the laboratory in order to determine the correlation between the UV absorbence and the measured parameter.

SUMMARY OF THE INVENTION

The present invention attempts to overcome the above-mentioned problems associated with the prior art, to provide an inexpensive and accurate monitor that can readily be used in a variety of locations.

The present invention provides a method of determining the amount of organic matter in a liquid sample comprising the steps of:
 (a) passing light of a wavelength in the UV region through the sample and sensing the emergent UV light intensity;
 (b) making a measurement to provide an indication of the absorption by the sample of visible light;
 (c) making a further measurement to provide an indication of the amount of scatter of light caused by the sample; and,
 (d) determining the amount of organic matter in the sample from the measured reduction in UV light intensity by a calculation in which the results from steps (b) and (c) are used for compensation purposes.

In contrast to known UV absorbence-based methods, the present method involves measuring both the amount of scatter caused by suspended solids in the liquid sample and the extent to which substances in the sample absorb visible light of one or more colours. Those results are then used for compensation purposes, i.e., to establish the reduction in the emergent UV light intensity that is due only to absorption by organic pollutants, so that the amount thereof in the sample can then be determined.

It has been discovered that particulate matter that is present in the liquid sample and that absorbs light in the visible part of the spectrum, also absorbs the UV light to such an extent as to contribute significantly to the measured reduction in intensity of the emergent UV light, and that the amount of light absorbed in the visible part of the spectrum can usefully be used to adjust the UV light absorption reading and give a more accurate indication of the amount of organic matter in the sample. Thus, whereas the natural background colour of a liquid has previously been disregarded, the present method involves measuring absorption in the visible region of the spectrum and adjusting the measured UV absorption in dependence upon that measurement, so that the amount of organic matter in the sample can be accurately and reliably assessed, regardless of the liquid quality. By compensating for the liquid background colour, the present method can be used to monitor liquid quality in a variety of locations, without the need for dilution of the liquid sample or for an initial calibration step.

The measurements in steps (a), (b) and (c) may be made either simultaneously, or sequentially, in any order. The measurements in steps (b) and (c) may be made either directly or indirectly. For example, the extent to which the sample absorbs the visible light may be determined by passing that light through the sample, measuring the emergent light intensity and using the measurement in step (c) to compensate for the reduction in intensity due to scatter, so as to determine the actual extent of absorption of the visible light.

Organic molecules give rise to absorption bands, as opposed to discrete lines, in the UV region. The UV absorption may therefore be measured at any wavelength at which the organic substances of interest absorb UV light, and preferably at one or more wavelengths at which that absorption is at a maximum. Unless a continuous UV source is used, however, the UV light will usually be generated at a single, suitable UV wavelength using a discrete light source; UV light of 254 nm wavelength may conveniently be generated by a mercury lamp and has been shown to give good results.

Preferably, the visible light is selected to be of one or more wavelengths that are highly absorbed by the sample.

The method may involve measuring visible light absorption at a number of different wavelengths spaced at intervals across the visible spectrum. Red, yellow and/or green wavelengths may be used, with yellow being preferred.

Step (c) enables the effect of non-organic suspended solids on the UV absorption measurement to be taken into account. It may conveniently comprise passing light through the liquid sample and measuring the amount of light scattered at a particular angle. The results of step (c) may also be used to calculate the amount of suspended solids in the sample.

Preferably, steps (a), (b) and (c) are carried out on the sample under the same conditions, for example, in the same measuring cell, so as to improve the accuracy of the results.

The liquid sample may be filtered prior to steps (a), (b) and (c), so as to prevent scattering by large solids from affecting the various light measurements and to minimize contamination of the various sensors and light sources employed. It is preferred, however, that the filtering should not remove particles of less than about 1 mm in diameter, with the use of a filter of mesh size not less that about 2 mm being especially preferred,
because otherwise fine suspended particles and associated material that contribute to the overall organic content measurement may also be inadvertently removed.

Usually, it will be necessary for the method to include an additional step of measuring one or more additional variable(s). The additional variable may also be measured for compensation purposes, as explained above. Preferably, the additional step will be carried out on the sample under the same conditions as steps (a), (b) and (c). The additional variable may be the emergent light intensity of UV light of a second wavelength, when such light is additionally passed through the liquid sample, the wavelength being a characteristic wavelength of a substance of interest, such as, for example, ammonia. One important variable that will normally need to be measured, at least for compensation purposes, is the liquid temperature, because variations in that temperature will affect the measured UV absorbence. In some applications, it may be desirable to measure pH and/or conductivity for compensation purposes. The effect of pH and conductivity on the measured UV absorbence is not fully understood. It has been shown that, for a constant organic content, a change in pH or conductivity will lead to a change in the measured UV absorbence.

Although the method may be used to determine TOC or COD, its most important application will be for determining the BOD of a liquid sample.

The present invention also provides apparatus suitable for use in all or part of a method as described above, which apparatus comprises first means for passing light of a wavelength in the UV region through the liquid sample and sensing the emergent UV light intensity, second means for making a measurement to provide an indication of the absorption by the sample of visible light, and third means for making a further measurement to provide an indication of the amount of scatter of visible light caused by the sample. Preferably, the apparatus includes processing means for use in step (d) for carrying out the calculation to determine the amount of organic matter.

The apparatus may conveniently be provided in a single housing and/or may be portable. The first, second and third means may be provided in a single measuring cell, so as to minimize errors caused due to local fluctuations, for example, in temperature.

Preferably, additional means will be provided for measuring one or more additional variables, as outlined above; the processing means may also use the measured additional variable for compensation purposes.

For most applications, the processing means are adapted to calculate the BOD of the sample.

As explained above, it is desirable for the apparatus not to be provided with a filter having a pore size of less than about 1 mm, and preferably not less than about 2 mm.

The present invention also provides sampling apparatus for withdrawing a sample from a liquid source having an open surface, which apparatus comprises a buoyant sampling head provided with an inlet port that communicates with a duct for connection to suction means, the apparatus being so arranged that, in use, the sampling head floats on the surface of the liquid source and the inlet port is disposed beneath that surface.

Such apparatus is substantially improved over prior art sampling apparatus, where sampling tends to be indiscriminate and blockage problems are usually encountered because of the suction employed. The use of the floating head ensures that the inlet port remains beneath the surface of the liquid source, thus preventing surface contaminants from blocking the inlet port or being drawn into the sampling apparatus. The immersion of the inlet port also means that it is exposed to the cleansing action of any liquid currents.

Preferably, a filter is disposed across the inlet port. Preferably, the filter has a convex surface so as to maximise the effect of the cleansing action of any liquid currents. Furthermore, it is preferred that the surface area of the filter is substantially larger than the average cross-sectional area of the duct, in order to present a larger surface area that is less likely to become blocked, even where substantial suction is employed.

The invention also provides a monitoring system for use in a method of determining the amount of organic matter in a liquid source, which system comprises monitoring apparatus as described earlier, in combination with the above described sampling apparatus.

Although the sampling apparatus is particularly suited for use with the above-described monitoring apparatus, especially where long-term and/or continuous monitoring of a liquid source is required, the sampling apparatus may also be employed with other types of monitoring or sensing equipment, in a variety of different applications.

BRIEF DESCRIPTION OF THE DRAWINGS

One form of organic pollutant monitor, and one type of sampling apparatus for use therewith, constructed in accordance with the invention, will now be described, by way of example only, with reference to the accompanying drawings, in which.

DETAILED DESCRIPTION OF EXEMPLARY EMBODIMENTS

Figure 1:
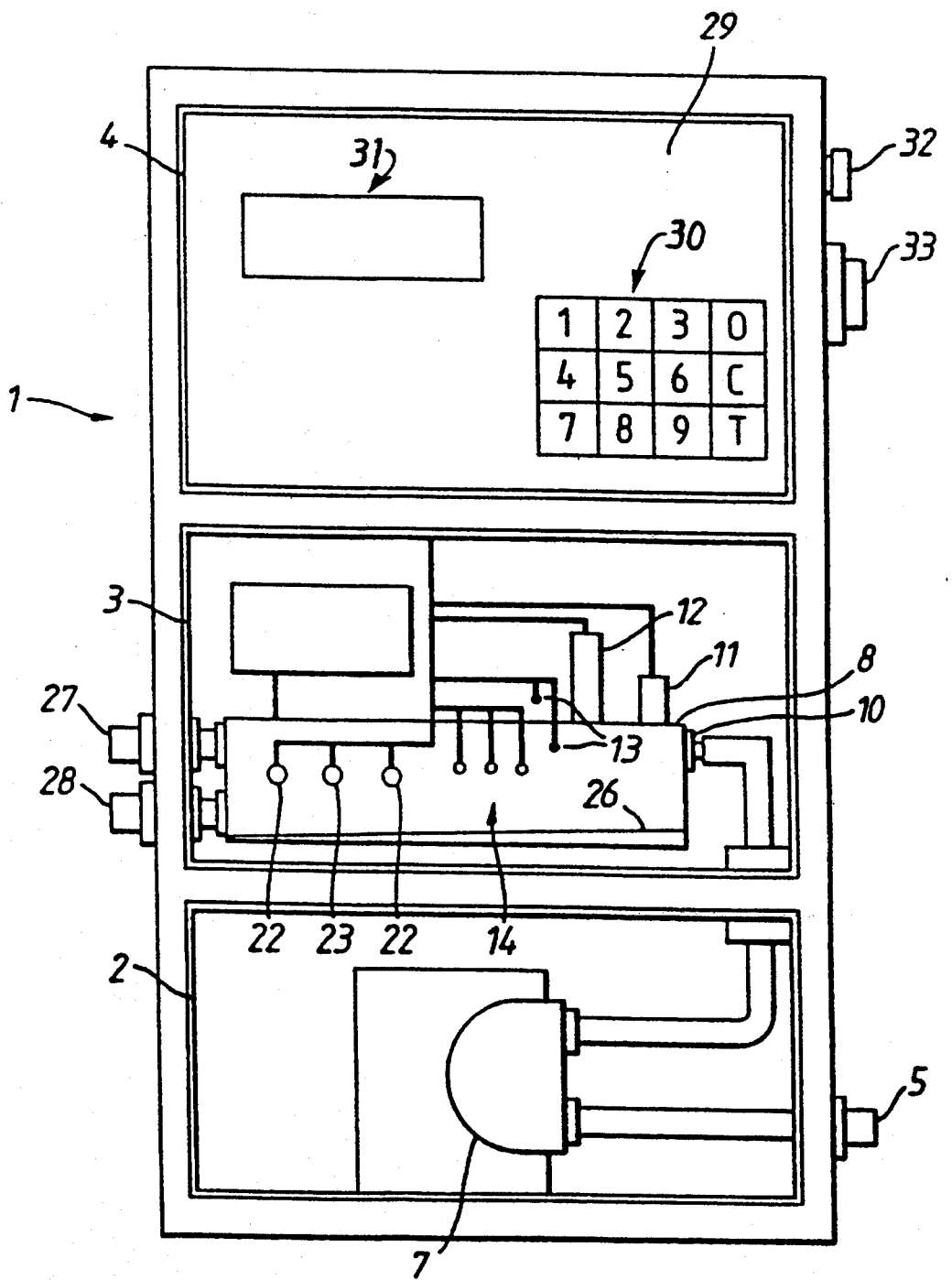
FIG. 1 is a partially cut-away schematic view of the monitor.
Figure 2:
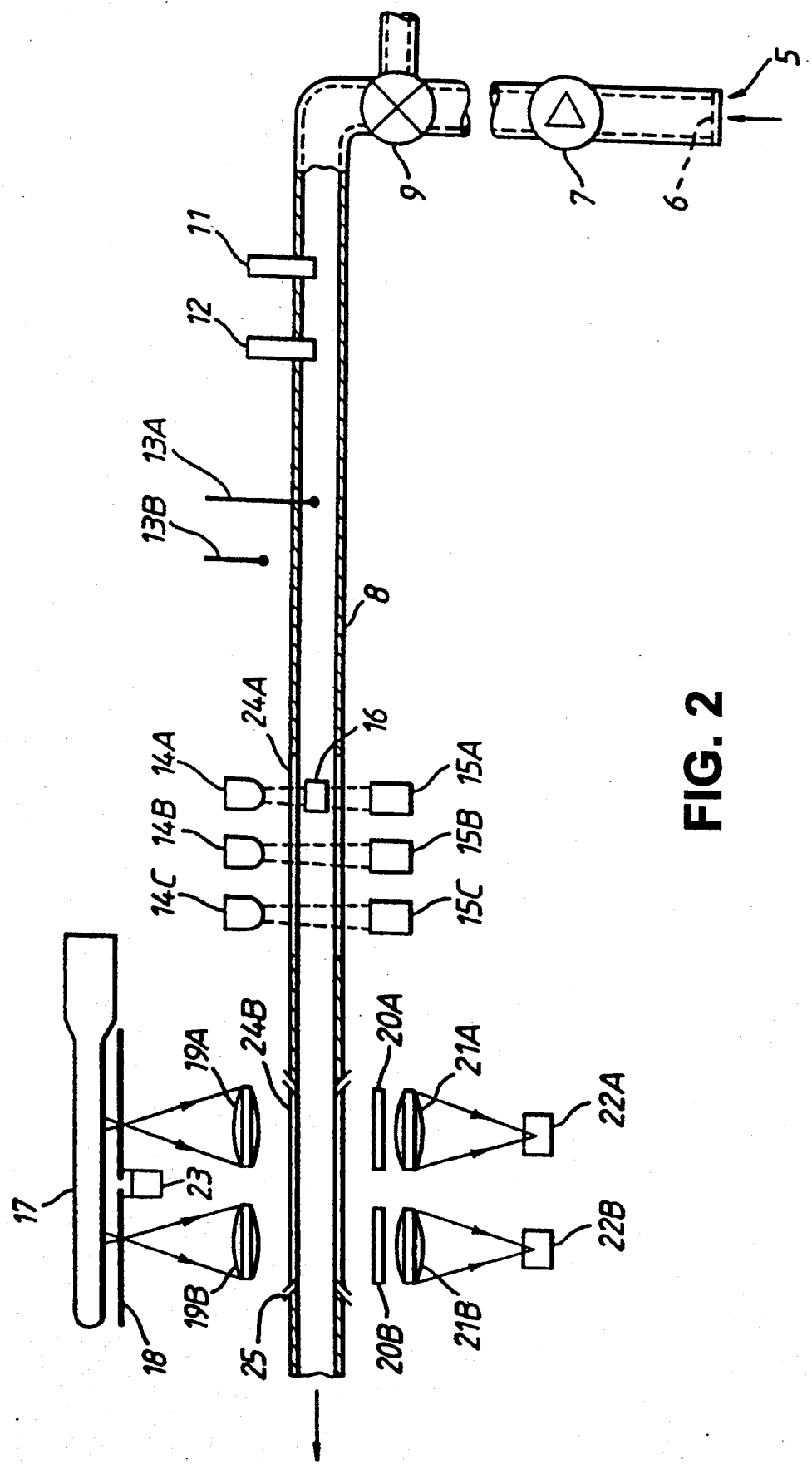
FIG. 2 is a schematic sectional view of the measuring cell of the monitor, to a larger scale than that of FIG. 1.

The organic pollutant monitor is capable of being used for on-line, continuous monitoring of liquid quality in a variety of on-site locations, such as, for example, rivers, reservoirs or industrial effluent outlets. The monitor 1 comprises a single, weatherproof, portable unit separated into three compartments 2, 3, 4 containing a pump, a measuring cell and sensors, and a microprocessor, respectively. In use, the monitor is attached to sampling apparatus 40, as described below.

The sampling apparatus is attached to an inlet port 5 of the device, across which port a filter 6 of 1 mm porosity is positioned. The inlet 5 is connected in the monitor by tubing of a suitable width to a suction pump 7.

The pump 7 is housed in a separate compartment, so as to avoid warming of the sensors. Further tubing connects the pump 7 to the measuring cell 8 in the central compartment 3. A multi-way valve 9 can optionally be provided for the purposes of backwashing or if dilution of the liquid sample is required.

In the central compartment 3, the measuring cell 8 is surrounded by an array of light sources and sensors. Nearest the inlet 10 of the cell is a conductivity probe 11, followed by a pH probe 12 and then two temperature probes 13A, 13B for measuring the liquid and ambient air temperature, respectively. Spaced a short distance therefrom are three light emitting diodes (LEDs) 14A, 14B, 14C, generating light of red, yellow and green wavelength, respectively. Three visible-sensitive silicon photodiodes 15A, 15B, 15C are arranged in corresponding, opposing positions on the other side of the measuring cell 8 to measure the emergent light intensity, with a fourth photodiode 16 occupying a position at right-angles to the red LED 14A, in order to measure the scatter produced by suspended solids or anything else in the liquid being sampled.

A tubular UV light source comprising a low pressure mercury lamp 17 is arranged along the remaining length of the measuring cell 8. The light intensity of the source 17 is selected so as not to cause warming or sterilization of the liquid sample since that could alter the BOD test result. An apertured screen 18 is arranged around the lamp 17 to produce two narrow beams of light. Two quartz (or fused silica) lenses 19A, 19B are positioned between the cell 8 and light source 17 to collimate the two light beams, and on the opposite side of the cell, two UV interference optical filters 20A, 20B are provided to separate out two wavelengths of interest. Receiving lenses 21A, 21B focus the selected emergent light rays onto two UV sensitive photodiodes 22A, 22B. An additional, visible-sensitive silicon photodiode 23 is positioned across one of the screen apertures to monitor the intensity of the UV light source 17.

In the vicinity of the UV and visible light sources, the measuring cell 8 has two optical windows 24A, 24B made of quartz (or fused silica) and associated cleaning means 25. The measuring cell 8 is also provided with a tapered channel wall 26 for facilitating manual cleaning, the width of which may be adjusted in order to alter the optical path length for example to allow for different ranges of measurements to be made. At the wider end of the cell, an outlet port 27 and cleaning port 28 are provided through which liquid can be introduced during manual cleaning. Automated cleaning facilities may also be provided in applications where frequent cleaning is necessary. Advantageously, wipers are inserted or installed for cleaning the optical windows.

Data from the various sensors is relayed to the microprocessor 29 in the third compartment 4. The microprocessor is connected to a numeric key pad 30 and a display 31 on a front panel of the monitor, although a RS232C communication port 32 is also provided for interfacing to additional hardware. Power is supplied to the monitor by means of an AC/DC socket 33 provided next to the communication port 32.

Figure 3:
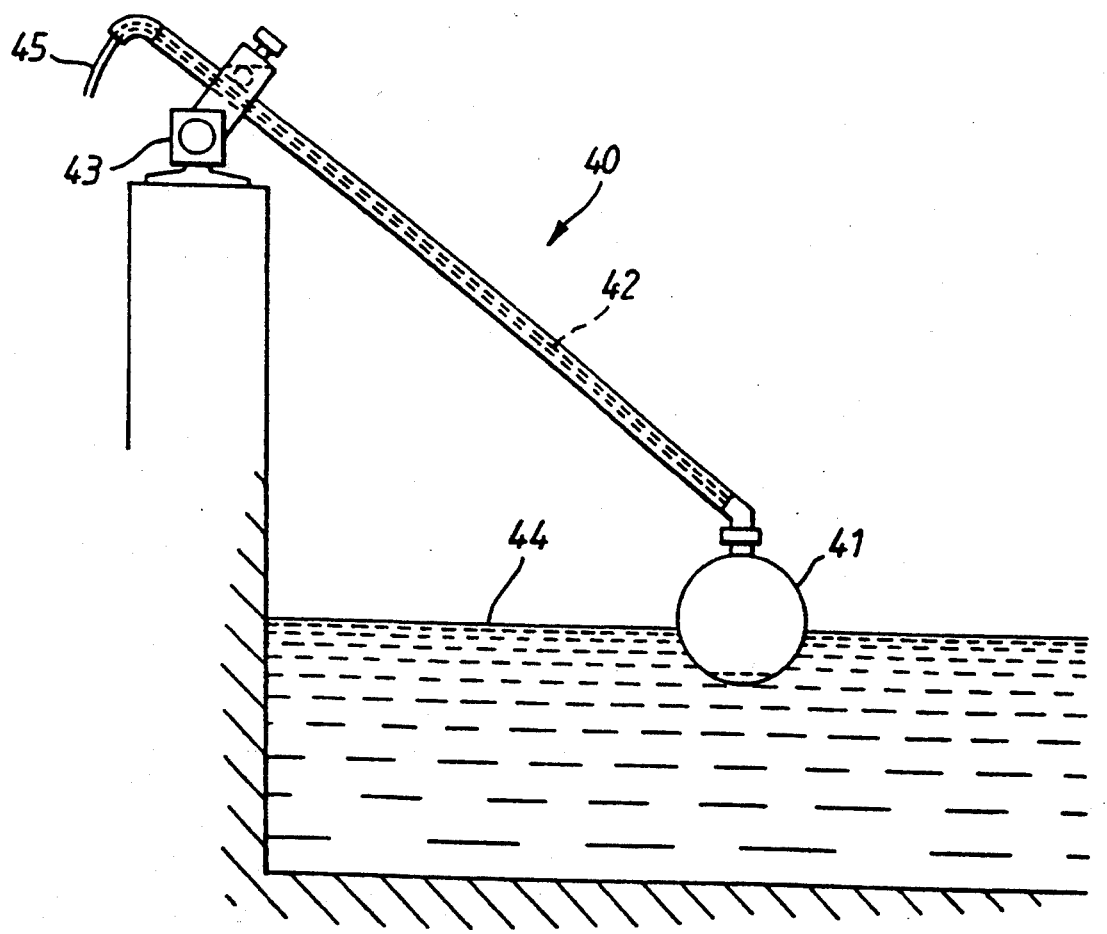
FIG. 3 is a side view of the sampling apparatus.
Figure 4A:
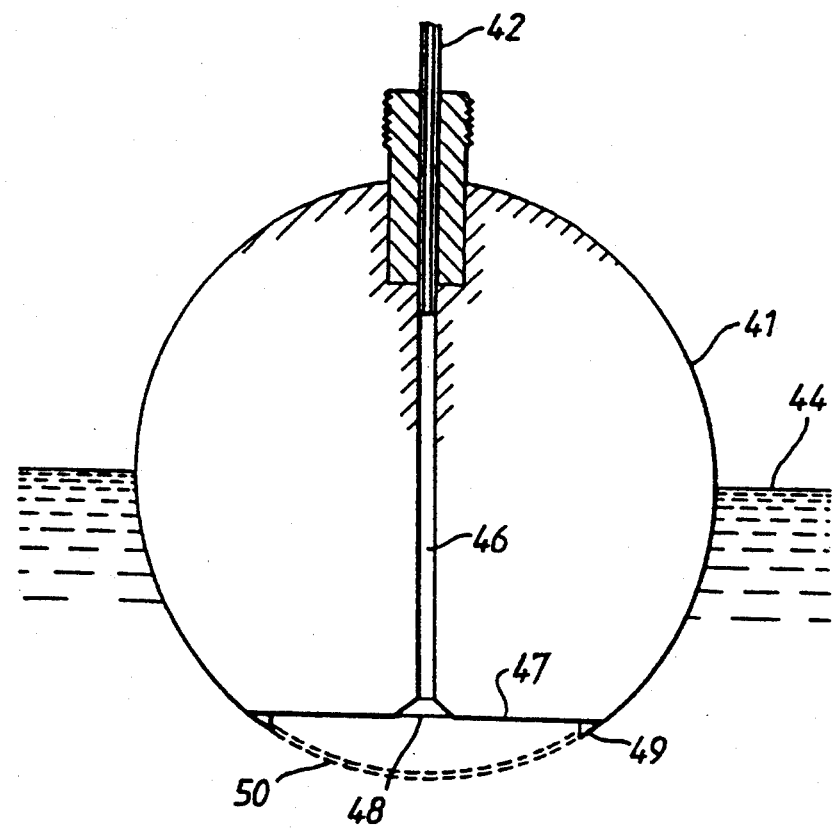
FIGS. 4a and 4b are, respectively, sectional and bottom views of the sampling head of the sampling apparatus.
Figure 4B:
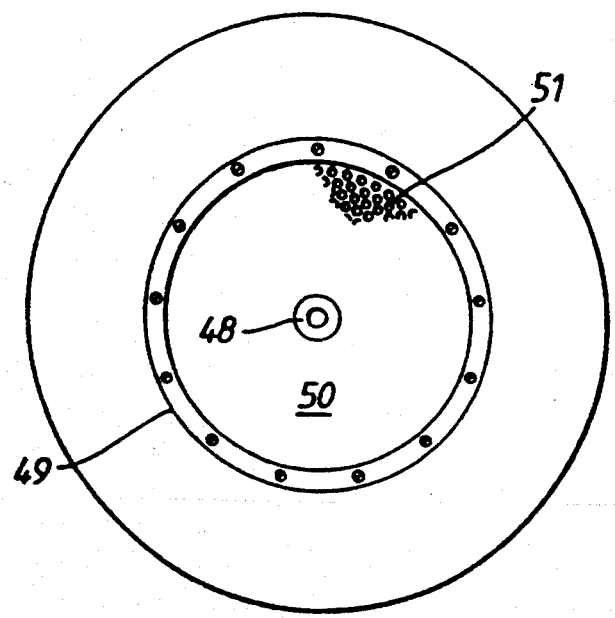

A sampling apparatus for use with the monitor in a location where the liquid source presents an open, accessible surface, is shown in FIGS. 3, 4a and 4b.

The sampling apparatus 40 comprises a buoyant sampling head 41 attached to the lower end of a pipe 42, the upper end of which is pivotally mounted on a support 43, which is raised above the surface 44 of the liquid source and disposed adjacent thereto. A flexible tube 45 leads from the upper end of the pipe 42 to the organic monitor 1.

The sampling head 41 comprises a hollow truncated sphere mounted on the lower end of the pipe 42 by means of a screw joint. Inside the sphere an internal pipe 46 leads from the joint to an end member 47, in which an inlet port 48 is provided. The end member 47 is sealingly secured to the rim 49 of the truncated end of the sphere, and is surrounded by a curved mesh 50 provided with 1 to 2 mm diameter holes 51 and also attached to the rim of the sphere.

When the monitor is operating, the pump draws liquid to be sampled into the sampling head 41 through the holes 51 of the mesh 50 and via the inlet port 48 into pipe 46 and then pipe 42. The pivotal mounting of the pipe 42 allows the sampling head 41 to float freely on the surface 44 of the liquid source, so that the inlet port 48 is always immersed. Thus, liquid is always withdrawn from beneath the surface 44, which may often be contaminated. Further, the mesh 50 presents a large surface area for filtering which, because of its immersed state, is to a large extent self-cleaning, this being especially the case where the liquid source is fast-flowing.

In use on site, the monitor can be set up for continuous, on-line operation, the sampling apparatus directing the liquid into the monitor. As will be explained below, the monitor may either be set up for immediate use, or may first be calibrated to provide a $BOD_5$ reading.

Liquid to be sampled is drawn into the monitor 1 at a volumetric rate of, for example, 1 liter per minute by the suction pump 7, passing through the coarse filter 6 where large solid particles, rags, etc., are removed. The liquid is then transported by the pump 7 to the measuring cell 8.

Inside the cell 8, the conductivity and pH probes 11, 12 measure the liquid quality for compensation purposes, as will be explained below. The temperature probes 13A, 13B measure the liquid and ambient air temperature, also for compensation purposes, as well as to enable the liquid temperature to be shown on the display 31.

Narrow beams of red, yellow and green light, from the light emitting diodes 14A, 14B, 14C, are transmitted through the first optical window 24A into the liquid sample. The intensity of the three emergent beams are measured by the three photodiodes 15A, 15B, 15C, and the measurements used for compensation purposes and to provide a displayable liquid colour reading. The fourth photodiode 16 detects the amount of red light scattered at 90° to the beam direction, to provide an indication of the concentration of suspended solids particles in the liquid sample. The amount of suspended solids is again displayable as well as being used for compensation purposes by the microprocessor.

The UV light source emits two UV light beams that are collimated by the lenses 19A, 19B and transmitted through the second cell optical window 24B, penetrating the liquid sample. The emergent light passes through the two interference filters 20A, 20B which separate out light of wavelength 254 nm and 310 nm, respectively, (the latter being a characteristic absorption wavelength of ammonia). The receiving lenses 21A, 21B focus that light onto the two UV sensitive photodiodes 22A, 22B, and the recorded light intensities, and hence, absorption at each of the two wavelengths is used to determine the level of organic matter and ammonia present in the sample, respectively, the ammonia concentration being used for compensation purposes and for the purpose of display.

The intensity of the UV source itself is continuously measured by the visible-sensitive photodiode (23) to ensure that the UV light intensity remains stable.

In the event that the monitor is being used for long-term, continuous monitoring, the monitor should be recalibrated at periodic intervals (eg monthly), in order to compensate for sensor drift due to associated fouling. Moreover, every six months or so the UV source should be replaced. Apart from that, however, the monitor does not have to be calibrated.

The microprocessor 29 processes the data received from the various sensors in order to determine the amount of colour-absorbing substances in the liquid, the temperature, suspended solids content, turbidity, ammonia content, pH and conductivity of the liquid. Each of those parameters can be displayed by operation of the key pad 30.

In contrast to existing monitors, the microprocessor calculates the amount of organic matter as a function of the measured UV emergent light intensity and by taking into account the effect of all of the above-mentioned parameters, of which the two most important parameters are the suspended solids content and the amount of colour-absorbing substances. The other parameters are of lesser importance, for the purposes of compensation in that, for most influent/effluent samples, they will not have as substantial effect on the UV absorbence; thus, in some applications it may be sufficient to compensate only for the suspended solids and red, yellow and green colours (or possibly only one of those colours).

The amount of organic matter is determined by means of a set of calculations which compensate for the effects of variation in temperature, pH and conductivity on the UV absorbence, and which also take into account the reduction in intensity of the emerging UV light due to the presence of suspended solids, coloured particles and absorbing ammonia molecules in the sample. The microprocessor is programmed to express the amount of organic matter in terms of BOD, TOC and COD. The BOD reading has been shown to correlate to an expected 5-day laboratory test BOD value ($BOD_5$) to an accuracy of greater than 0.93, for a wide range of sample types. If desired, however, the monitor could be calibrated before use to produce a $BOD_5$ reading, by performing the 5 day laboratory test on a liquid sample and comparing the $BOD_5$ reading obtained with that previously given by the monitor.

By compensating for all the factors that are liable to affect the UV absorbence, as mentioned above, the monitor is able to produce results of an accuracy not previously achieved by existing UV absorption-based monitors. Moreover, the present monitor can be used in a variety of locations regardless of the effluent quality. It may, however, be desirable for the monitor to be adapted to dilute samples, for example, when monitoring highly contaminated samples.

Another factor found to have a very significant effect on the UV absorbence measurement is the extent of filtration. It has been discovered that fine filtration removes fine suspended particles and associated material that contribute to the overall organic content measurement, hence leading to readings of soluble BOD only, whereas both soluble and non-soluble BOD would be recorded in the 5-day BOD test. Thus, it is highly preferred that only a coarse filter of 1 to 2 mm porosity is used, so as to exclude, for example, gross solids and rags from internal pipework, but without preventing the passage of BOD (solids).

The monitor may be modified to suit particular applications. For example, where it is desired to monitor the presence of a compound other than ammonia, the 310 nm interference filter could be replaced or supplemented with an alternative filter adapted to select the characteristic wavelength of that other compound; in that case, it may be necessary to provide a different UV light source for example, a deuterium lamp providing a continuous spectrum from 200 to 320 nm. Similarly, the choice of visible light wavelengths will depend on which types of light-absorbing substances are present in the liquid being sampled. Where the same monitor is to be used for a wide range of samples it may be desirable to provide more than one sensing arrangement to measure any one variable; for example it may be useful to have two UV sensing arrangements both operating at 254 nm but differing in that one is suitable for use with cleaner liquids of relatively low absorption and the other for dirtier liquids of relatively high absorption. The two sensing arrangements may differ in the intensity of the light source, the sensitivity of the sensor, the separation of the sensor and source or in some other similar way. The apparatus may be arranged with appropriate electronic controls to enable it to switch automatically to the correct sensing arrangement according to the dirtiness of the sample. The same principle can be applied to the other sensing arrangements, for example the visible light sensing arrangements.

We claim:

1. A method of determining the amount of organic matter in a liquid sample comprising the steps of:
   (a) passing light of a wavelength in the UV region through the sample and sensing the emergent UV light intensity;
   (b) making a measurement to provide an indication of the absorption by the sample of visible light;
   (c) making a further measurement to provide an indication of the amount of scatter of light caused by the sample; and
   (d) determining the amount of organic matter in the sample from the measured reduction in UV light intensity by a calculation in which the results from steps (b) and (c) are used for compensation purposes.

2. A method as claimed in claim 1, wherein UV light of 254 nm wavelength is used in step (a).

3. A method as claimed in claim 1, wherein the visible light is selected to be of one or more wavelengths that are highly absorbed by the sample.

4. A method as claimed in claim 1, wherein the visible light is selected to be of yellow wavelength.

5. A method as claimed in claim 1, wherein step (c) comprises passing light through the liquid sample and measuring the amount of light scattered at a particular angle.

6. A method as claimed in claim 1, wherein steps (a), (b) and (c) are carried out on the sample under the same conditions.

7. A method as claimed in claim 6, including an additional step of measuring one or more additional variable(s) and wherein the additional step is carried out on the sample under the same conditions as steps (a), (b) and (c).

8. A method as claimed in claim 1, wherein the liquid sample is filtered prior to steps (a), (b) and (c).

9. A method as claimed in claim 8, wherein the filtering does not remove particles of less than about 1 mm.

10. A method as claimed in claim 1, including an additional step of measuring one or more additional variable(s).

11. A method as claimed in claim 10, wherein the additional variable is measured for compensation purposes.

12. A method as claimed in claim 10, wherein an additional variable is the emergent light intensity of UV light of a second wavelength.

13. A method as claimed in claim 12, wherein the second wavelength corresponds to a characteristic absorption wavelength of ammonia.

14. A method as claimed in claim 10, wherein an additional variable is the temperature of the liquid.

15. A method as claimed in claim 10, wherein an additional variable is the pH of the liquid.

16. A method as claimed in any one of claim 10, wherein an additional variable is the conductivity of the liquid.

17. A method as claimed in claim 10, wherein the BOD of the liquid sample is determined.

18. Apparatus for determining the amount of organic matter in a liquid sample, the apparatus comprising first means for passing light of a wavelength in the UV region through the liquid sample and sensing the emergent UV light intensity, second means for making a measurement to provide an indication of the absorption by the sample of visible light, and third means for making a further measurement to provide an indication of the amount of scatter if light caused by the sample including means for measuring one or more additional variables.

19. Apparatus for determining the amount of organic matter in a liquid sample, the apparatus comprising first means for passing light of a wavelength in the UV region through the liquid sample and sensing the emergent UV light intensity, second means for making a measurement to provide an indication of the absorption by the sample of visible light, and third means for making a further measurement to provide an indication of the amount of scatter of light caused by the sample.

20. Apparatus as claimed in claim 19, including processing means for determining the amount of organic matter in the sample from an output of the first means, adjusted in accordance with outputs from the second and third means.

21. Apparatus as claimed in claim 20, wherein the processing means uses the measured additional variable for compensation purposes.

22. Apparatus as claimed in claim 20 wherein the processing means are adapted to calculate the BOD of the sample.

23. Apparatus as claimed in claim 19, wherein the apparatus is contained in a single housing and/or is portable.

24. Apparatus as claimed in claim 19, wherein the first, second and third means are provided in a single measuring cell.

25. Apparatus as claimed in claim 19, wherein the apparatus is not provided with a filter having a pore size of less than about 1 mm.

26. A monitoring system for use in a method of determining the amount of organic matter in a liquid source, which system comprises apparatus as claimed in claim 19 in combination with sampling apparatus for withdrawing a sample from a liquid source having an open surface, which sampling apparatus comprises a buoyant sampling head provided with an inlet port that communicates with a duct for connection to suction means, the sampling apparatus being so arranged that, in use, the sampling head floats on the surface of the liquid source and the inlet port is disposed beneath that surface.

27. A monitoring system as claimed in claim 26, wherein a filter is disposed across the inlet port.

28. A monitoring system as claimed in claim 27, wherein the surface area of the filter is substantially larger than the average cross-sectional area of the duct.

29. The use of a monitoring system as claimed in claim 26 in a method of determining the amount of organic matter in a liquid source.

30. The use as claimed in claim 29 of a monitoring system, wherein the system is used on a long-term and/or continuous basis.

* * * * *